United States Patent [19]

Cook

[11] 4,315,000
[45] Feb. 9, 1982

[54] β-D-ARABINOFURANOSYLIMIDAZO(4,5-C)PYRIDINE COMPOUNDS AND METHODS FOR THEIR PRODUCTION

[75] Inventor: P. Dan Cook, Ann Arbor, Mich.

[73] Assignee: Warner-Lambert Company, Morris Plains, N.J.

[21] Appl. No.: 166,867

[22] Filed: Jul. 7, 1980

[51] Int. Cl.³ .................. A61K 31/70; C07H 19/06; C07H 19/08; C07H 19/10

[52] U.S. Cl. .................. 424/180; 424/24; 424/26; 424/27; 424/28

[58] Field of Search ............. 536/24, 26, 27, 28; 424/180

[56] References Cited

U.S. PATENT DOCUMENTS

| | | | |
|---|---|---|---|
| 3,472,838 | 10/1969 | Haressian | 536/24 |
| 3,501,456 | 3/1970 | Shen | 536/24 |
| 3,651,045 | 3/1972 | Haskell et al. | 536/24 |
| 3,703,507 | 11/1972 | Haskell et al. | 536/24 |
| 4,048,432 | 9/1977 | Baker | 536/26 |
| 4,055,717 | 10/1977 | Baker | 536/24 |
| 4,056,674 | 11/1977 | Robins et al. | 536/24 |
| 4,069,382 | 1/1978 | Baker | 536/26 |

FOREIGN PATENT DOCUMENTS

| | | |
|---|---|---|
| 1386584 | 3/1975 | United Kingdom . |
| 1474299 | 5/1977 | United Kingdom . |
| 1562899 | 3/1980 | United Kingdom . |

OTHER PUBLICATIONS

Poonian et al., J. Med. Chem., 22, 958 (1979).
Cook et al., J. Am. Chem. Soc., 98, 1492 (1976).
Glandeman et al., J. Org. Chem., 28, 3004 (1963).

*Primary Examiner*—Blondel Hazel
*Attorney, Agent, or Firm*—Walter Patton

[57] ABSTRACT

Hydroxy, amino and sulfhydryl derivatives of 1-β-D-arabinofuranosyl-1H-imidazo[4,5-c]pyridine, their corresponding esters and non-toxic pharmaceutically acceptable salts are produced by arabinofuranosylation of the requisite heterocycles with 2,3,5-tri-O-benzyl-α-D-arabinofuranosyl halide and further reaction to obtain the desired compounds. These water soluble compounds are resistant to adenosine deaminase and exhibit antiviral activity.

26 Claims, No Drawings

β-D-ARABINOFURANOSYLIMIDAZO(4,5-c)PYRIDINE COMPOUNDS AND METHODS FOR THEIR PRODUCTION

SUMMARY AND DETAILED DESCRIPTION

The present invention relates to novel 1-β-D-arabinofuranosyl-1H-imidazo[4,5-c]pyridines that are useful antiviral agents and to the method for their production. More particularly, the invention relates to novel hydroxy, amino and sulfhydryl derivatives of 1-β-D-arabinofuranosyl-1H-imidazo[4,5-c]-pyridine compounds that are represented by the formula

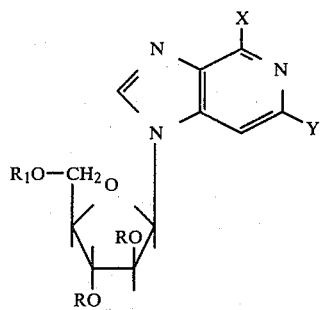

and the pharmaceutically acceptable salts thereof wherein when Y is hydrogen or $NH_2$, X is $NH_2$, OH or SH; R is hydrogen or acyl containing 2 or 3 carbon atoms; and $R_1$ is hydrogen, acyl containing 2 or 3 carbon atoms or phosphate.

Included in the present invention are compounds having the structural formula:

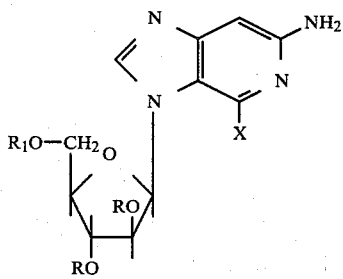

and the pharmaceutically acceptable salts thereof wherein X is OH or $NH_2$; R is hydrogen or acyl containing 2 or 3 carbon atoms; and $R_1$ is hydrogen, acyl containing 2 or 3 carbon atoms or phosphate.

The preferred compounds of the present invention are designated:
1-β-D-arabinofuranosyl-1H-imidazo[4,5-c]pyridin-4-amine;
1-β-D-arabinofuranosyl-1H-imidazo[4,5-c]pyridin-4-amine 5'-phosphate;
1-β-D-arabinofuranosyl-1,5-dihydro-4H-imidazo[4,5-c]pyridin-4-one;
1-β-D-arabinofuranosyl-1,5-dihydro-4H-imidazo[4,5-c]pyridine-4-one 5'-phosphate;
1-β-D-arabinofuranosyl-1,5-dihydro-4H-imidazo[4,5-c]pyridine-4-thione;
1-(2,3,5-tri-O-acetyl-β-D-arabinofuranosyl)-1H-imidazo[4,5-c]pyridin-4-amine;
6-amino-1-β-D-arabinofuranosyl-1,5-dihydro-4H-imidazo[4,5-c]pyridin-4-one;
6-amino-1-β-D-arabinofuranosyl-1,5-dihydro-4H-imidazo[4,5-c]pyridin-4-one 5'-phosphate;
6-amino-3-β-D-arabinofuranosyl-3,5-dihydro-4H-imidazo[4,5-c]pyridin-4-one;
6-amino-3-β-D-arabinofuranosyl-3,5-dihydro-4-H-imidazo[4,5-c]pyridin-4-one 5'-phosphate;
1-β-D-arabinofuranosyl-4,6-diamino-1H-imidazo[4,5-c]pyridine;
1-β-D-arabinofuranosyl-4,6-diamino-1H-imidazo[4,5-c]pyridine 5'-phosphate;
3-β-D-arabinofuranosyl-4,6-diamino-3H-imidazo[4,5-c]pyridine;
3-β-D-arabinofuranosyl-4,6-diamino-3H-imidazo[4,5-c]pyridine 5'-phosphate;
6-amino-1-β-D-arabinofuranosyl-1,5-dihydro-4H-imidazo[4,5-c]pyridine-4-thione; and the
pharmaceutically acceptable salts thereof.

In accordance with the invention, compounds having the formula

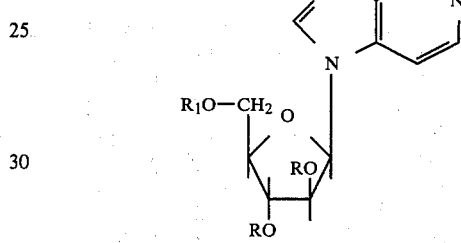

wherein X, R and $R_1$ are as defined above are produced by treating 4-chloro-1H-imidazo[4,5-c]pyridine with sodium hydride in a suitable solvent to form the anion having the formula

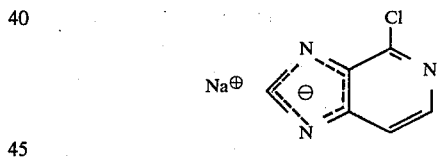

and glycosylating said anion with 2,3,5-tri-O-benzyl-α-D-arabinofuranosyl chloride.

The resulting blocked 4-chloronucleoside is converted to the corresponding blocked 4-amino-β-D-arabinofuranosylnucleoside by treatment with excess hydrazine to form the corresponding 4-hydrazino derivative. The crude 4-hydrazinonucleoside, without any purification, is hydrogenolyzed with Raney nickel to produce the corresponding blocked 4-aminonucleoside. The blocking groups are removed by conventional means such as reduction with sodium in liquid ammonia. Recrystallization from water provides the desired unblocked 4-aminonucleoside.

The 4-aminonucleoside is converted to the 2,3,5-tri-O-acetyl compound; the 5'-phosphate compound; and the 1,5-dihydro-4H-imidazo[4,5-c]pyridin-4-one compound by treatment with acetic anhydride, phosphoryl chloride in triethylphosphate, and sodium nitrite respectively. The 4-aminonucleoside 5'-phospate is treated with sodium nitrite to produce the corresponding 1,5-dihydro-4-H-imidazo[4,5-c]pyridin-4-one 5'-phosphate.

The 1-β- and 3-β-arabinofuranosyl derivatives of 3-deazaguanine are produced by a base catalyzed ring closure of the corresponding methyl 5- and 4-cyanomethyl-1-(2,3,5-tri-O-benzyl-β-D-arabinofuranosyl)imidazole-4 and 5-carboxylates respectively. The blocking groups are removed by conventional means such as reduction with sodium in liquid ammonia. The corresponding 5'-phosphates are produced by treatment with phosphoryl chloride in triethyl phosphate.

The required methyl 5- and 4-cyanomethyl-1-(2,3,5-tri-O-benzyl-β-D-arabinofuranosyl)imidazole-4 and 5-carboxylates are produced by the arabinofuranosylation of the anion of methyl 4(5)-cyanomethylimidazole-5(4)-carboxylate with 2,3,5-tri-O-benzyl-α-D-arabinofuranosyl chloride and separating and collecting the β-anomers. Said anion is formed by the treatment of methyl 4(5)-cyanomethylimidazole-5(4)-carboxylate with a strong base such as sodium hydride in DMF.

The 1-β and 3-β-arabinofuranosyl derivatives of 4,6-diamino-1H and 3H-imidazo[4,5-c]pyridine are produced by a base catalyzed ring closure of the corresponding 4-cyano-5-cyanomethyl-1- and 5-cyano-4-cyanomethyl-3-(2,3,5-tri-O-benzyl-β-D-arabinofuranosyl)-imidazoles. The O-benzyl blocking groups are removed by conventional means such as reduction with sodium in liquid ammonia and palladium on carbon and hydrogen. The corresponding 5'-phosphates are produced by treatment with phosphoryl chloride in triethyl phosphate.

The required 4-cyano-5-cyanomethyl-1- and 5-cyano-4-cyanomethyl-3-(2,3,5-tri-O-benzyl-β-D-arabinofuranosyl)imidazoles are produced by the arabinofuranosylation of the anion of 5(4)-cyano-4(5)-cyanomethylimidazole and separating and collecting the β-anomers. Said anion is formed by the treatment of 5(4)-cyano-4-(5)-cyanomethylimidazole with a strong base such as sodium hydride in DMF.

The heterocycles required as starting material in the foregoing process can be prepared by any of a variety of methods. This general class of compounds and a number of individual members of the class have been reported.

The 4-chloro-1H-imidazo[4,5-c]pyridine is described in R. J. Rousseau and R. K. Robins, *J. Heterocyclic Chem.*, 2, 196 (1965). The methyl 1H-5-cyanomethyl-1-H-imidazole-4-carboxylate is described in P. D. Cook, et al., *J. Am. Chem. Soc.*, 98 1492 (1976); and the 4-cyano-5-cyanomethyl-1H-imidazole is described in R. J. Rousseau, et al., *J. Heterocyclic Chem.*, 11, 233 (1974).

The requisite sugar, 2,3,5-tri-O-benzyl-α-D-arabinofuranosyl chloride is prepared according to C. P. J. Glaudemans, et al., *J. Am. Chem. Soc.* 87, 4636 (1965).

Pharmaceutically acceptable salts can be produced by dissolving the nucleosides in water containing one equivalent of the appropriate acid. The aqueous solution is concentrated in vacuo and the residue is recrystallized from ethanol-water mixtures.

The products of the phosphorylation reactions set forth above may be isolated in the free acid form or in salt form by appropriate adjustment of the pH with a suitable base. The initial free acid product is first adsorbed on activated charcoal and then converted to the diammonium salt by eluting the charcoal with a solvent mixture made up of ethanol, water, and ammonium hydroxide. The diammonium salt can then be converted back to the free acid by ion exchange techniques, or it can be converted to other salts by direct reaction with suitable salt forming substances. The free acid 1-β-D-arabinofuranosyl-1H-imidazo[4,5-c]pyridine 5'-phosphate can also be converted to other salts by direct reaction with a suitable base.

The various salts comprehended within the present invention include those formed with the ammonium ion, alkali metal cations, and alkaline earth metal cations. These salts and the free acid β-D-arabinofuranosylimidazo[4,5-c]pyridine 5'-phosphate may differ in certain physical properties, but they are otherwise equivalent for purposes of the invention.

The amino, hydroxy, and sulfhydryl derivatives of β-D-arabinofuranosylimidazo[4,5-c]pyridine and their sugar esters are novel chemical compounds that are useful as antiviral agents against Herpes virus.

Their activity as antiviral agents can be quantitatively measured in an in vitro test by utilizing the plaque reduction technique first developed by Dulbecco (Proc. Natl. Acad. Sci., Volume 38, pages 747–752) and modified by Hsiung and Melnick [Virology, Volume I, pages 533–535 (1955)]. In this test, a complete cell monolayer is first grown on a glass test unit. The growth medium is then removed, and the virus is adsorbed on the cell monolayer for a measured time period. In the absence of an antiviral agent, the virus will destroy well-defined areas of cells, called plaques, that can be seen microscopically when the vital stain, neutral red, is added to the system. To test the inhibiting effect of a given compound, the test compound in solution is added to the virus-cell system, and the whole is covered with a nutrient agar overlay containing neutral red. After incubation, the plaques are counted, and the number of plaques produced in the system containing the test compound is compared with the number produced in the control systems, from which only the test compound is omitted. The inhibitory activity of a test compound is reported as the percentage reduction of the plaque count on the test units compared with that on the controls.

When tested by this plaque reduction technique, with 4 oz. glass bottles serving as the test units and H. Ep. No. 2 cells making up the cell monolayer, the preferred compounds of the invention, in Hank's Balanced Salt Solution (pH 7-8), typically are found to give substantial plaque reduction against Herpes simplex.

The compounds of the present invention are administered parenterally, preferably intravenously. Injectable solutions are given so as to provide the host with from 0.0005 mg to 5 mg of the compound of this invention per kg of body weight per day. The preferred quantity which is administered on a daily basis is from about 0.005 mg to 2 mg of the compound of this invention per kg of body weight.

The pharmaceutical composition may be in bulk form containing 0.005 to 2 parts of the compound of this invention which is placed in solution at time of use by the addition of a solvent which is appropriate for injectables. In the alternative, the pharmaceutical composition may be an aqueous solution containing 0.005 to 2 parts of the compound of this invention and other materials such as preservatives, buffering agents, agents intended to adjust the isotonicity of the solution, etc. The volume of water is not critical and may vary from less than 1 ml to about 500 ml.

In addition, the compounds of the present invention may be employed in ophthalmic compositions, such as ointments and solutions, in the treatment of Herpes keratitis. Thus ointments or solutions containing about 0.001 to 0.5 percent, preferably 0.001 to 0.05 percent of the compound of this invention in a suitable pharmaceutical carrier may be employed. In addition, preservatives, agents intended to adjust isotonicity of the solution, buffers, etc., may be incorporated into the pharmaceutical carriers.

Lastly, the compounds of the present invention may also be employed in topical ointments and creams. The ointment or cream should contain about 0.001 to 0.5 percent, preferably 0.001 to 0.05 percent of the compound of this invention in a suitable pharmaceutical carrier which may optionally contain perservatives, coloring agents, etc.

The invention is illustrated by the following examples.

EXAMPLE 1

1-β-D-Arabinofuranosyl-1H-imidazo[4,5-c]pyridin-4-amine

4-Chloro-1-(2,3,5-tri-O-benzyl-β-D-arabinofuranosyl)-imidazo[4,5-c]pyridine

A solution of 2.4 g of sodium hydride, 15.4 g of 4-chloro-1H-imidazo[4,5-c]pyridine, and 200 ml of dry dimethylformamide (DMF) is stirred at 50° C. for 5 minutes, cooled, and added to 43.9 g of 2,3,5-tri-O-benzyl-α-D-arabinofuranosyl chloride. The solution is kept at ambient temperature for two hours, concentrated in vacuo, and distributed between a mixture of ethyl acetate-water. Chromatography of the dried ethyl acetate layer over silica gel with 4:1 benzene-ethyl acetate provides 49.6 g of syrupy 4-chloro-1-(2,3,5-tri-O-benzyl-β-D-arabinofuranosyl)imidazo[4,5-c]-pyridine.

1-(2,3,5-Tri-O-benzyl-β-D-arabinofuranosyl)imidazo[4,5-c]pyridin-4-amine

A mixture of 18.0 g of 4-chloro-1-(2,3,5-tri-O-benzyl-β-D-arabinofuranosyl)imidazo[4,5-c]pyridine and 200 ml of 97% hydrazine is heated under reflux and a nitrogen atmosphere for 0.5 hour. The excess hydrazine is removed by evaporation in vacuo and the dark residue is co-evaporated several times with xylenes providing a syrupy residue which is dissolved in ethyl acetate and extracted with water. The ethyl acetate is removed in vacuo affording the hydrazide in the form of a dark syrup which is dissolved in a 400 ml of a 50% aqueous ethanol solution and treated with 50 g of Raney nickel. The mixture is heated under reflux with stirring for one hour, filtered and the filtrate evaporated in vacuo providing 13.9 g of 1-(2,3,5-tri-O-benzyl-β-D-arabinofuranosyl)imidazo[4,5-c]pyridin-4-amine in the form of a red syrup.

1-β-D-Arabinofuranosyl-1H-imidazo[4,5-c]pyridin-4-amine

To a solution of 13.7 g of 1-(2,3,5-tri-O-benzyl-β-D-arabinofuraosyl)imidazo[4,5-c]pyridin-4-amine in 500 ml of liquid ammonia is added portionwise 4 g of sodium with stirring. The suspension is stirred for 1.5 hours, treated with 10 g of ammonium chloride, and allowed to evaporate in a stream of nitrogen. The residue is triturated with ether, cold water, and recrystallized from water (charcoal) to afford 5.2 g of 1-β-D-arabinofuranosyl-1H-imidazo[4,5-c]pyridin-4-amine in the form of white needles, m.p.: dec > 280° C. with prior browning; dec. pt. 297°–298° C. (after drying at 100° C. for 2 hours): $[\alpha]_D^{25} = 20.2°$ (1.06%, 1N HCl).

EXAMPLE 2

1-(2,3,5-Tri-O-acetyl-β-D-arabinofuranosyl)imidazo[4,5-c]pyridin-4-amine

A solution of 1.5 g of 1-β-D-arabinofuranosyl-1H-imidazo[4,5-c]pyridin-4-amine, 1.9 g of acetic anhydride, 67 ml of pyridine, and 37 mg of p-dimethylaminopyridine is stirred at 0° C. for 6 hours, treated with 50 ml of ethanol, and evaporated in vacuo. The residue is co-evaporated with xylenes, dissolved in ethyl acetate, extracted with water, and dried with MgSO4. Recrystallization of the dried residue from ethanol provides 1-(2,3,5-tri-O-acetyl-β-D-arabinofuranosyl)imidazo[4,5-c]pyridin-4-amine.

EXAMPLE 3

1-β-D-Arabinofuranosyl-1,5-dihydro-4H-imidazo-[4,5-c]pyridin-4-one

A solution of 1.5 g of 1-β-D-arabinofuranosyl-1H-imidazo[4,5-c]pyridin-4-amine, 6 ml of acetic acid, 150 ml of water, and 2.67 g of sodium nitrite is kept at ambient temperature for 8 hours, treated with 2.4 g of urea, and then with 50 ml of wet Dowex 50 1×8 (H+), and concentrated to dryness in vacuo. The residue is co-evaporated several times with xylenes and then recrystallized from water to provide 1-β-D-arabinofuranosyl-1,5-dihydro-4H-imidazo[4,5-c]pyridin-4-one.

EXAMPLE 4

1-β-D-Arabinofuranosyl-1H-imidazo[4,5-c]pyridin-4-amine 5′-Phosphate

A mixture of 4 g of 1-β-D-arabinofuranosyl-1H-imidazo-[4,5-c]pyridin-4-amine, 40 ml of triethylphosphate, and 2.55 g of phosphoryl chloride is stirred at 0°–5° C. for 3 hours at which point an additional one g of phosphoryl chloride is added and stirring at 0° C.–5° C. is continued for 3 hours. The solution is poured into 150 ml of crushed ice and the pH is adjusted by the addition of solid sodium hydrogen carbonate until it stabilizes at 5–6. The solution is extracted with chloroform and concentrated in vacuo until crystallization begins. Enough water is added to achieve solution and the pH is adjusted to 6–7 with solid sodium hydrogen carbonate. The solution is placed on a Dowex 1×2 50–100 mesh (formate) column (200 ml of wet resin) and is washed with water until the eluate is salt-free. Gradient elution (water to 0.1 M formic acid) gives the pure product. The appropriate fractions are evaporated in vacuo, keeping the temperature below 30° C., to a small volume. Addition to hot ethanol, until the cloud point is obtained, allows crystallization to proceed several hours later providing 1-β-D-arabinofuranosyl-1H-imidazo-[4,5-c]pyridin-4-amine 5′-phosphate.

EXAMPLE 5

1-β-D-Arabinofuranosyl-1,5-dihydro-4H-imidazo-[4,5-c]pyridine-4-thione

A solution of 3.0 g of 1-β-D-arabinofuranosyl-1,5-dihydro-4H-imidazo[4,5-c]pyridin-4-one, eight ml of acetic anhydride, 150 ml of pyridine, and 50 mg of p-dimethylaminopyridine is stirred at room temperature for 24 hours, evaporated in vacuo, co-evaporated with xylenes, and distributed between water and ethyl acetate. The ethyl acetate layer is washed with saturated NaHCO3 and dried with MgSO4. Removal of the ethyl acetate provides 1-(2,3,5-tri-O-acetyl-β-D- arabinofuranosyl)-1,5-dihydro-4H-imidazo[4,5-c]pyridin-4-one. This is dissolved in 150 ml of dry pyridine, treated with 8.8 g phosphorus pentasulfide, and heated under reflux for 5 hours. The pyridine is removed in vacuo and the residue is treated with water. The precipitate is filtered, washed with water, and recrystallized from ethanol to afford 1-(2,3,5-tri-O-acetyl-β-D-arabinofuranosyl)-1,5-dihydro-4H-imidazo-[4,5-c]pyridine-4-thione.

A solution of 5.0 g of 1-(2,3,5-tri-O-acetyl-β-D-arabinofuranosyl)-1,5-dihydro-4H-imidazo[4,5-c]pyridine-4-thione, 200 ml of methanol, and 54 mg of sodium metholate is heated under reflux for 2 hours and treated with IRC-50 ion exchange resin. The filtrate is evaporated in vacuo and the resulting residue is recrystallized from ethanol-water to provide 1-β-D-arabinofuranosyl-1,5-dihydro-4H-imidazo[4,5-c]pyridine-4-thione.

EXAMPLE 6

1-β-D-Arabinofuranosyl-1,5-dihydro-4H-imidazo[4,5-c]-pyridin-4-one 5'-Phosphate

A solution of 3.46 g of 1-β-D-arabinofuranosyl-1H-imidazo[4,5-c]pyridin-4-amine 5'-phosphate, 6 ml of acetic acid, 100 ml of water, and 3.45 g of sodium nitrite is stirred at 0° for 3 hours and then at ambient temperature for 10 hours. The solution is treated with 3.0 g of urea and then 100 ml of wet Dowex 50 1×8 (H+), and evaporated in vacuo to dryness. Recrystallization of the residue from ethanol-water provides 1-β-D-arabinofuranosyl-1.5-dihydro-4H-imidazo-[4,5-c]pyridin-4-one 5'-phosphate.

EXAMPLE 7

6-Amino-1-β-D-arabinofuranosyl-1,5-dihydro-4H-imidazo-[4,5-c]pyridin-4-one

Arabinofuranosylation of methyl 4(5)-cyanomethylimidazole-5(4)-carboxylate

A solution of 1.2 g of sodium hydride, 8.25 of methyl 4(5)-cyanomethylimidazole-5(4)-carboxylate prepared according to the process of P.D. Cook, et al., *J. Am. Chem. Soc.*, 98, 1492 (1976), and 100 ml of dimethyl formamide is stirred at 50° for one minute, cooled, and added to 22.0 g of 2,3,5-tri-O-benzyl-α-D-arabinofuranosyl chloride. The solution is kept at ambient temperature for 2 hours, concentrated in vacuo, and distributed between a mixture of ethyl acetate-water. Chromatography of the dried (MgSO4) ethyl acetate layer over silica gel with benzene-ethyl acetate (4:1) provides 4.8 g methyl 5-cyanomethyl-1-(2,3,5-tri-O-benzyl-β-D-arabinofuranosyl)imidazole-4-carboxylate. (R$_f$ 0.13) and 20.0 g methyl 4-cyanomethyl-1-(2,3,5-tri-O-benzyl-β-D-arabinofuranosyl)-imidazole-5-carboxylate (R$_f$ 0.73) in the form of syrups.

6-Amino-1-(2,3,5-tri-O-benzyl-β-D-arabinofuranosyl)-1,5-dihydro-4H-imidazo[4,5-c]pyridin-4-one A mixture of 12.5 g of methyl 5-cyanomethyl-1-(2,3,5-tri-O-benzyl-β-D-arabinofuranosyl)imidazole-4-carboxylate and 50 ml of liquid ammonia is placed in a stainless steel bomb and heated in a steam bath for 20 hours. The ammonia is allowed to evaporate and the residue dissolved in chloroform and placed on a column of silica gel (250 g packed in chloroform-methanol, 20:1). Elution with chloroform-methanol (20:1) provides 9.2 g of 6-amino-1-(2,3,5-tri-O-benzyl-β-D-arabinofuranosyl)-1,5-dihydro-4H-imidazo[4,5c]-pyridin-4-one.

6-Amino-1-β-D-arabinofuranosyl-1,5-dihydro-4H-imidazo[4,5-c]pyridin-4-one

A mixture of 7.5 g of 6-amino-1-(2,3,5-tri-O-benzyl-β-D-arabinofuranosyl)-1,5-dihydro-4H-imidazo[4,5-c]-pyridin-4-one, 1.5 g of 20% palladium on carbon, 6.4 ml of acetic acid, and 150 ml of methoxy-ethanol is hydrogenated at 50° C. and ca 3 atmospheres until uptake of hydrogen ceases. The mixture is filtered, evaporated in vacuo, dissolved in water, and treated with 50 ml of wet IR-45 ion exchange resin. The filtrate is concentrated to dryness in vacuo and recrystallized from ethanol-water to provide 3.2 g of 6-amino-1-β-D-arabinofuranosyl-1,5-dihydro-4H-imidazo[4,5-c]pyridin-4-one.

EXAMPLE 8

6-Amino-1-β-D-arabinofuranosyl-1-5-dihydro-4H-imidazo-[4,5-c]pyridin-4-one 5'-Phosphate A mixture of 2.6 g of 6-amino-1-β-D-arabinofuranosyl-1,5-dihydro-4H-imidazo[4,5-c]pyridin-4-one, 5.64 g of phosphoryl chloride, and 25 ml of triethyl phosphate is stirred at 0°-5° C. for 10 hours. The solution is added dropwise to a vigorously stirred flask of anhydrous ether (500 ml). The ether is decanted and additional ether (300 ml) is added to the beige precipitate. After stirring for 0.5 hour, the ether is decanted, and this procedure is repeated with additional ether (300 ml). The precipitate is filtered, washed with ether, and then dissolved in ice water (ca 60 g). The aqueous solution is allowed to stand at room temperature overnight, adjusted to pH 8 with 1 N sodium hydroxide, and placed on a column of Bio-Rad AG 1×8 (formate form, 50-100 mesh, 30 ml of wet resin). After washing with water (300 ml), the column is eluted with a gradient of 0.2 to 0.5 M formic acid (500 ml each). Fractions containing the product are pooled and reduced to a small volume in vacuo. Addition of ethanol precipitated the product which is filtered, washed with ethanol and ether, and dried under vacuum at 100° C. for 2 hours to provide 1.3 g of 6-amino-1-β-D-arabinofuranosyl-1,5-dihydro-4H-imidazo[4,5-c]pyridin-4-one 5'-phosphate.

EXAMPLE 9

6-Amino-3-β-D-arabinofuranosyl-3,5-dihydro-4H-imidazo[4,5-c]pyridin-4-one

6-Amino-3-(2,3,5-tri-O-benzyl-β-D-arabinofuranosyl)-3,5-dihydro-4H-imidazo[4,5-c]pyridin-4-one A mixture of 8.4 g of methyl 4-cyanomethyl-1-(2,3-5-tri-O-benzyl-β-D-arabinofuranosyl)imidazole-5-carboxylate and 20 ml of liquid ammonia is placed in a stainless steel bomb (40 ml) and heated in a steam bath for 10 hours. The ammonia is evaporated in a stream of nitrogen and the residue is dissolved in chloroform and placed on a column of silica gel (250 g packed in chloroform methanol, 20:1). Elution with the same solvent system provides 6.6 g of 6-amino-3-(2,3,5-tri-O-benzyl-β-D-arabinofuranosyl)-3,5-dihydro-4H-imidazo[4,5-c]pyridin-4-one in the form of a syrup.

6-Amino-3-β-D-arabinofuranosyl-3,5-dihydro-4H-imidazo[4,5-c]pyridin-4-one

A mixture of 5.9 g of 6-amino-3-(2,3,5-tri-O-benzyl-β-D-arabinofuranosyl)-3,5-dihydro-4H-imidazo-[4,5-c]pyridin-4-one, one g of 20% palladium on carbon, 5 ml of acetic acid, and 95 ml of methoxyethanol is hydrogenated at 50° C. and ca 3 atmospheres until hydrogen uptake ceases, the mixture is filtered, evaporated in vacuo, and co-evaporated with xylenes to provide a syrup which is dissolved in water and treated with 50 ml of wet IR-45 ion exchange resin. The resin is filtered, washed several times with boiling water and the combined filtrates are evaporated in vacuo to provide 2.5 g of crude product. Recrystallization from ethanol-water provides 0.42 g of 6-amino-3-β-D-arabinofuranosyl-3,5-dihydro-4H-imidazo[4,5-c]pyridin-4-one.

EXAMPLE 10

6-Amino-3-β-D-arabinofuranosyl-3,5-dihydro-4H-imidazo-[4,5-c]pyridin-4-one 5'-Phosphate A mixture of 2.6 g of 6-amino-3-β-D-arabinofuranosyl-3,5-dihydro-4H-imidazo[4,5-c]pyridin-4-one, 5.64 g of phosphoryl chloride, and 25 ml of triethyl phosphate is stirred at 0°-5° C. for 5 hours and added to a vigorously stirred flask of anhydrous ether (500 ml). The ether is decanted and additional ether (300 ml) is added to the beige precipitate. After stirring 0.5 hour, the ether is decanted, and this procedure is repeated with additional ether (300 ml). The precipitate is filtered, washed with ether, and dissolved in ice-water (ca. 60 g). The aqueous solution is allowed to stand at ambient temperature overnight, adjusted to pH 8 with 1 N sodium hydroxide, and placed on a column of Bio-Rad AG 1×8 (formate form, 50–100 mesh, 30 ml of wet resin). After washing with water (300 ml), the column is eluted with a gradient of 0.2 to 0.5 M formic acid (500 ml each). Fractions containing the product are pooled and reduced to a small volume in vacuo. Addition of ethanol precipitates 6-amino-3-β-D-arabinofuranosyl-3,5-dihydro-4H-imidazo[4,5-c]pyridin-4-one 5'-phosphate which is filtered, washed with ethanol and ether, and dried under vacuum at 100° for 2 hours.

EXAMPLE 11

1-β-D-arabinofuranosyl-1H-4,6-Diaminoimidazo-[4,5-c]pyridine

Arabinosylation of 5(4)cyano-4(5)-cyanomethylimidazole

A solution of 1.2 g of sodium hydride, 6.6 g of 4(5)-cyano-5(4)-cyanomethylimidazole prepared by the process of R. J. Rousseau, et al., J. Heterocyclic Chem., 11, 233 (1974), and 100 ml of DMF is stirred at 50° C. for one minute, cooled, and added to 22.0 g of 2,3,5-tri-O-benzyl-α-D-arabinofuranosyl chloride. The solution is kept at ambient temperature for 2 hours, concentrated in vacuo, and distributed between a mixture of ethyl acetatewater. Chromatography of the dried (MgSO$_4$) ethyl acetate layer over silica gel with benzene-ethyl acetate (4:1) provides 4-cyano-5-cyanomethyl-1-(2,3,5-tri-O-benzyl-β-D-arabinofuranosyl)-imidazole and 5-cyano-4-cyanomethyl-3-(2,3,5-tri-O-benzyl-β-D-arabinofuranosyl)imidazole.

4,6-Diamino-1-(2,3,5-tri-O-benzyl-β-D-arabinofuranosyl)imidazo[4,5-c]pyridine

A mixture of 6.0 g of 4-cyano-5-cyanomethyl-1-(2,3,5-tri-O-benzyl-β-D-arabinofuranosyl)imidazole and 300 ml of dry methanol saturated at 0° C. with ammonia is kept in a steel bomb at ambient temperatures for 24 hours and then evaporated in vacuo to dryness. The residue is triturated with ether, dissolved in methanol, absorbed on silica gel, and chromatographed over silica gel with chloroform-methanol (10:1) to provide 4.0 g of 4,6-diamino-1-(2,3,5-tri-O-benzyl-β-D-arabinofuranosyl)imidazo[4,5-c]pyridine.

1-β-D-Arabinofuranosyl-4,6-diamino-1H-imidazo-[4,5-c]pyridine

A mixture of 5.0 g of 4,6-diamino(2,3,5-tri-O-benzyl-β-D-arabinofuranosyl)imidazo[4,5-c]pyridine, 1.5 g of 20% palladium on carbon, 1.6 ml of acetic acid, and 150 ml of methoxyethanol is hydrogenated at 50° C. and ca. 3 atmospheres until uptake of hydrogen ceases. The mixture is filtered, evaporated in vacuo, dissolved in water, and treated with 50 ml of wet IR-45 ion exchange resin. The filtrate is concentrated to dryness in vacuo and recrystallized from ethanol-water to provide 2.1 g of 1-β-D-arabinofuranosyl-4,6-diamino-1H-imidazo-[4,5-c]pyridine.

EXAMPLE 12

1-β-D-Arabinofuranosyl-4,6-diamino-1H-imidazo[4,5-c]-pyridine 5'-Phosphate

A mixture of 4 g of 1-β-D-arabinofuranosyl-4,6-diamino-1H-imidazo[4,5-c]pyridine, 40 ml of triethyl phosphate, and 2.55 g of phosphoryl chloride (POCl$_3$) is stirred at 0° to 5° C. for 3 hours at which time an additional one g of POCl$_3$ is added and stirring at 0° to 5° is continued for 3 hours. The solution is poured into 150 ml of crushed ice and the pH is adjusted by the addition of solid sodium hydrogen carbonate until it stabilizes at pH 5–6. The solution is extracted with chloroform and concentrated in vacuo until crystallization begins. Water is added to achieve solution and the pH is adjusted to 6–7 with NaHCO$_3$. The solution is placed on a Dowex 1×2, 50–100 mesh (formate) column (200 ml of wet resin) and is washed with water until the eluate is salt-free. The column is then gradient eluted (water to 0.1 M formic acid). The appropriate fractions containing the product are evaporated in vacuo to a small volume, keeping the temperature below 30° C. Addition of hot ethanol until the cloud point is obtained allows crystallization of 1-β-D-arabinofuranosyl-4,6-diamino-1H-imidazo[4,5-c]-pyridine 5'-phosphate.

EXAMPLE 13

3-β-D-Arabinofuranosyl-4,6-diamino-3H-imidazo-[4,5-c]pyridine 4,6-Diamino-3-(2,3,5-tri-O-benzyl-β-D-arabinofuranosyl)-3H-imidazo[4,5-c]pyridine A mixture of 5.0 g of 5-cyano-4-cyanomethyl-3-(2,3,5-tri-O-benzyl-D-arabinofuranosyl)imidazole, 15 ml of liquid ammonia, and 15 ml of methanol is heated in a steel bomb at 125°–135° C. for 16 hours. The reaction solution was evaporated in vacuo to dryness. The residue is absorbed on silica gel with the aid of methanol and chromatographed over silica gel with chloroform-methanol (10:1) to provide 4,6-diamino-3-(2,3,5-tri-O-benzyl-β-D-arabinofuranosyl)-3H-imidazo[4,5-c]pyridine.

3-β-D-Arabinofuranosyl-4,6-diamino-3H-imidazo[4,5-c]-pyridine

A mixture of 5.0 g of 4,6-diamino-3-(2,3,5-tri-O-benzyl-β-D-arabinofuranosyl)-3H-imidazo[4,5-c]pyridine, 1.5 g of 20% palladium on carbon, 1.6 ml of acetic acid and 150 ml of methoxyethanol is hydrogenated at 50° C. and ca. 3 atmospheres until uptake of hydrogen ceases.

The mixture is filtered, evaporated in vacuo, dissolved in water, and treated with 50 ml of wet IR-45 ion exchange resin. The filtrate is concentrated to dryness and recrystallized from ethanol-water to provide 2.0 g of 3-β-D-arabinofuranosyl-4,6-diamino-3H-imidazo-[4,5-c]pyridine.

EXAMPLE 14

3-β-D-Arabinofuranosyl-4,6-diamino-3H-imidazo-[4,5-c]pyridine 5'-Phosphate

The title compound is prepared by the process of Example 12 wherein 1-β-D-arabinofuranosyl-4,6-diamino-1H-imidazo[4,5-c]pyridine is replaced by an equal amount of 3-β-D-arabinofuranosyl-3H-imidazo[4,5-c]pyridine.

EXAMPLE 15

6-Amino-1-β-D-arabinofuranosyl-1,5-dihydro-4H-imidazo[4,5-c]pyridine-4-thione

6-Amino-1,5-dihydro-1-(2,3,5-tri-O-benzyl-β-D-arabinofuranosyl)-4H-imidazo[4,5-c]pyridine-4-thione A mixture of 8 g of 4-cyano-5-cyanomethyl-1-(2,3,5-tri-O-benzyl-β-D-arabinofuranosyl)imidazole, 250 ml of ethanol saturated at 0° C. with hydrogen sulfide, and 2.5 g of triethylamine is kept in a steel bomb for 48 hours at ambient temperature. The reaction solution is evaporated in vacuo to a yellow foam which is coevaporated with ethanol several times to provide 6-amino-1,5-dihydro-1-(2,3,5-tri-O-benzyl-β-D-arabinofuranosyl)-4H-imidazo[4,5-c]pyridine-4-thione.

6-Amino-1-β-D-arabinofuranosyl-1,5-dihydro-4H-imidazo[4,5-c]pyridine-4-thione

To a solution of 8.0 g of 6-amino-1,5-dihydro-1-(2,3,5-tri-O-benzyl-β-D-arabinofuranosyl)-4H-imidazo-[4,5-c]pyridine-4-thione, and 300 ml of liquid ammonia is added portionwise 3 g of sodium with stirring. The suspension is stirred for 1.5 hours, treated with ammonium chloride and allowed to evaporate in a stream of nitrogen. The residue is triturated with ether, cold water, and recrystallized from water to provide. 6-amino-1-β-D-arabinofuranosyl-1,5-dihydro-4H-imidazo[4,5-c]pyridine-4-thione.

I claim:

1. The compound having the structural formula:

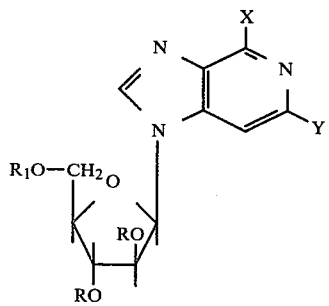

and the pharmaceutically acceptable salts thereof wherein when Y is hydrogen or NH₂, X is NH₂, OH or SH; R is hydrogen or acyl containing 2 or 3 carbon atoms; and R₁ is hydrogen, acyl containing 2 or 3 carbon atoms or phosphate.

2. The compound having the structural formula:

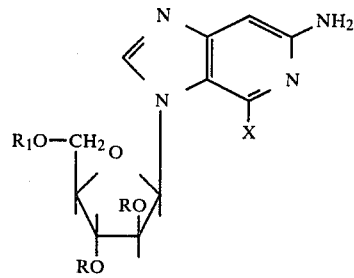

and the pharmaceutically acceptable salts thereof wherein X is OH or NH₂; R is hydrogen or acyl containing 2 or 3 carbon atoms; and R₁ is hydrogen, acyl containing 2 or 3 carbon atoms or phosphate.

3. The compound according to claim 1 designated 1-β-D-arabinofuranosyl-1H-imidazo[4,5-c]pyridin-4-amine and the pharmaceutically acceptable salts thereof.

4. The compound designated 1-β-D-arabinofuranosyl-1H-imidazo[4,5-c]pyridin-4-amine 5'-phosphate and the pharmaceutically acceptable salts thereof.

5. The compound according to claim 1 designated 1-β-D-arabinofuranosyl-1,5-dihydro-4H-imidazo[4,5-c]-pyridin-4-one and the pharmaceutically acceptable salts thereof.

6. The compound designated 1-β-D-arabinofuranosyl-1,5-dihydro-4H-imidazo[4,5-c]-pyridine-4-one 5'-phosphate and the pharmaceutically acceptable salts thereof.

7. The compound according to claim 1 designated 1-β-D-arabinofuranosyl-1,5-dihydro-4H-imidazo[4,5-c]pyridine-4-thione and the pharmaceutically acceptable salts thereof.

8. The compound according to claim 1 designated 1-(2,3,5-tri-O-acetyl-β-D-arabinofuranosyl)-1H-imidazo-[4,5-c]pyridin-4-amine and the pharmaceutically acceptable salts thereof.

9. The compound according to claim 1 designated 6-amino-1-β-D-arabinofuranosyl-1,5-dihydro-4H-imidazo-[4,5-c]pyridin-4-one and the pharmaceutically acceptable salts thereof.

10. The compound designated 6-amino-1-β-D-arabinofuranosyl-1,5-dihydro-4H-imidazo-[4,5-c]pyridin-4-one 5'-phosphate and the pharmaceutically acceptable salts thereof.

11. The compound according to claim 2 designated 6-amino-3-β-D-arabinofuranosyl-3,5-dihydro-4H-imidazo-[4,5-c]pyridin-4-one and the pharmaceutically acceptable salts thereof.

12. The compound designated 6-amino-3-β-D-arabinofuranosyl-3,5-dihydro-4H-imidazo-[4,5-c]pyridin-4-one 5'-phosphate and the pharmaceutically acceptable salts thereof.

13. The compound according to claim 1 designated 1-β-D-arabinofuranosyl-4,6-diamino-1H-imidazo[4,5-c]-pyridine and the pharmaceutically acceptable salts thereof.

14. The compound designated 1-β-D-arabinofuranosyl-4,6-diamino-1H-imidazo[4,5-c]-pyridine 5'-phosphate and the pharmaceutically acceptable salts thereof.

15. The compound according to claim 2 designated 3-β-D-arabinofuranosyl-4,6-diamino-3H-imidazo[4,5-c]-pyridine and the pharmaceutically acceptable salts thereof.

16. The compound designated 3-β-D-arabinofuranosyl-4,6-diamino-3H-imidazo[4,5-c]-pyridine 5'-phosphate and the pharmaceutically acceptable salts thereof.

17. The compound according to claim 1 designated 6-amino-1-β-D-arabinofuranosyl-1,5-dihydro-4H-imidazo-[4,5-c]pyridine-4-thione and the pharmaceutically acceptable salts thereof.

18. An improved process for producing a compound of the formula

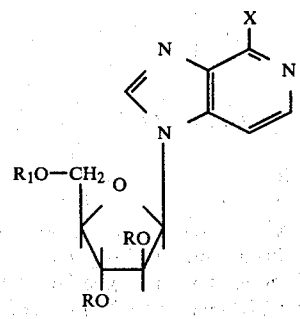

wherein X is NH₂, OH or SH; R is hydrogen or acyl containing 2 or 3 carbon atoms; and R₁ is hydrogen, acyl containing 2 or 3 carbon atoms or phosphate which comprises β-D-arabinofuranosylating 4-chloro-1H-imidazo-[4,5-c]pyridine with 2,3,5-tri-O-benzyl-α-D-arabinofuranosyl chloride; treating the resulting blocked nucleoside sequentially with hydrazine, Raney nickel and sodium in liquid ammonia to obtain 1-β-D-arabinofuranosyl-1H-imidazo[4,5-c]pyridin-4-amine and acylating, phosphorylating, treating with sodium nitrate then phosphorus pentasulfide to obtain the desired compounds wherein the improvement comprises treating 4-chloro-1H-imidazo[4,5-c]pyridine with sodium hydride in a suitable solvent to form the anion having the formula

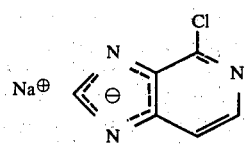

and β-D-arabinofuranosylating said anion with 2,3,5-tri-O-benzyl-α-D-arabinofuranosyl chloride.

19. An improved process for producing a compound of the formula

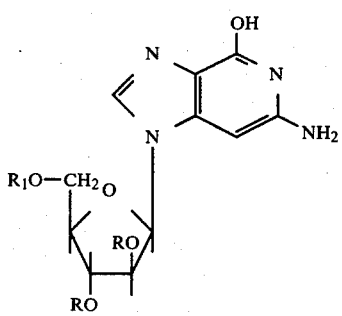

wherein R is hydrogen or acyl containing 2 or 3 carbon atoms; and R₁ is hydrogen, acyl containing 2 or 3 carbon atoms or phosphate which comprises β-D-arabinofuranosylating methyl 4(5)-cyanomethylimidazole-5(4)-carboxylate with 2,3,5-tri-O-benzyl-α-D-arabinofuranosyl chloride; separating and collecting the β-anomers; treating the resulting blocked nucleoside with sodium in liquid ammonia to obtain 6-amino-1,5-dihydro-1-β-D-arabinofuranosyl-4H-imidazo[4,5-c]pyridin-4-one and acylating or phosphorylating to obtain the desired compounds wherein the improvement comprises treating methyl 4(5)-cyanomethylimidazole-5(4)-carboxylate with sodium hydride in a suitable solvent to form the anion having the formula

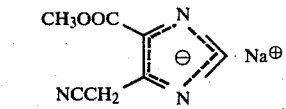

β-D-arabinofuranosylating said anion with 2,3,5-tri-O-benzyl-α-D-arabinofuranosyl chloride.

20. An improved process for producing a compound of the formula

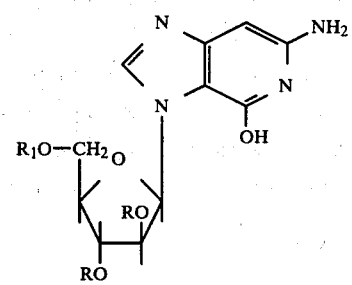

wherein R is hydrogen or acyl containing 2 or 3 carbon atoms; and R₁ is hydrogen, acyl containing 2 or 3 carbon atoms or phosphate which comprises β-D-arabinofuranosylating methyl 4(5)-cyanomethylimidazole-5(4)-carboxylate with 2,3,5-tri-O-benzyl-α-D-arabinofuranosyl chloride; separating and collecting the β-anomers; treating the resulting blocked nucleoside with sodium in liquid ammonia to obtain 6-amino-3-β-D-arabinofuranosyl-3,5-dihydro-4H-imidazo[4,5-c]pyridin-4-one and acylating or phosphorylating to obtain the desired compounds wherein the improvement comprises treating methyl 4(5)-cyanomethylimidazole-5(4)-carboxylate with sodium hydride in a suitable solvent to form the anion having the formula

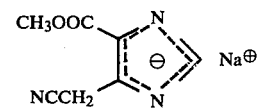

and β-D-arabinofuranosylating said anion with 2,3,5-tri-O-benzyl-α-D-arabinofuranosyl chloride.

21. An improved process for producing compounds of the formula wherein R is hydrogen or acyl containing 2 or 3 carbon atoms; R₁ is hydrogen, acyl containing 2 or 3 carbon atoms or phosphate which comprises β-D-arabinofuranosylating 4(5)-cyano-5(4)-cyanomethylimidazole with 2,3,5-tri-O-benzyl-α-D-arabinofuranosyl chloride; separating and collecting the β-anomers; treating the resulting blocked nucleoside with sodium in liquid ammonia to obtain 1-β-D-arabinofuranosyl-4,6-diamino-1H-imidazo[4,5-c]pyridine and acylating or phosphorylating to obtain the desired compounds wherein the improvement comprises treating 4(5)-cyano-5(4)-cyanomethylimidazole with sodium hydride in a suitable solvent to form the anion having the formula and β-D-arabinofuranosylating said anion with 2,3,5-tri-O-benzyl-α-D-arabinofuranosyl chloride.

22. An improved process according to claim 21 for producing compounds of the formula wherein R is hydrogen or acyl containing 2 or 3 carbon atoms; and R₁ is hydrogen, acyl containing 2 or 3 carbon atoms or phosphate which comprises β-D-arabinofuranosylating 4(5)-cyano-5(4)-cyanomethylimidazole with 2,3,5-tri-O-benzyl-α-D-arabinofuranosyl chloride, separating and collecting the β-anomers; treating the resulting blocked nucleoside with sodium in liquid ammonia to obtain 3-β-D-arabinofuranosyl-4,6-diamino-3H-imidazo[4,5-c]pyridine and acylating or phosphorylating to obtain the desired compounds wherein the improvement comprises treating 4(5)-cyano-5(4)-cyanomethylimidazole with sodium hydride in a suitable solvent to form the anion having the formula and β-D-arabinofuranosylating said anion with 2,3,5-tri-O-benzyl-α-D-arabinofuranosyl chloride.

23. An antiviral composition comprising an effective amount of the compounds of claim 1 and a pharmaceutically acceptable carrier.

24. An antiviral composition comprising an effective amount of the compounds of claim 2 and a pharmaceutically acceptable carrier.

25. A method of treating Herpes simplex viral infection in a host by the administration of an effective amount of the compound according to claim 1.

26. A method of treating Herpes simplex viral infection in a host by the administration of an effective amount of the compound according to claim 2.

* * * * *